(12) United States Patent
Digby et al.

(10) Patent No.: US 6,704,596 B2
(45) Date of Patent: Mar. 9, 2004

(54) ELECTRICALLY ACTIVE MEDICAL IMPLANT

(75) Inventors: Dennis Digby, Wilsonville, OR (US); Max Schaldach, deceased, late of Erlangen (DE), by Max Schaldach, Jr., legal representative

(73) Assignee: Biotronik Mess- und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 297 days.

(21) Appl. No.: 09/963,108

(22) Filed: Sep. 25, 2001

(65) Prior Publication Data

US 2002/0062137 A1 May 23, 2002

(30) Foreign Application Priority Data

Sep. 26, 2000 (DE) .......................................... 100 48 648

(51) Int. Cl.$^7$ ................................................. A61N 1/08
(52) U.S. Cl. ................................ 607/2; 607/5; 607/34; 607/29
(58) Field of Search ........................ 607/2, 5, 16, 27, 607/29, 34; 320/166; 429/61

(56) References Cited

U.S. PATENT DOCUMENTS

| | | |
|---|---|---|
| 5,285,779 A | 2/1994 | Cameron |
| 5,814,075 A | 9/1998 | Kroll |
| 5,876,423 A | 3/1999 | Braun |
| 5,949,632 A | 9/1999 | Barraras, Sr. |
| 6,008,625 A | 12/1999 | Gan |
| 6,044,295 A | 3/2000 | Pilz |
| 6,091,989 A | 7/2000 | Swerdlow |

FOREIGN PATENT DOCUMENTS

| | | |
|---|---|---|
| DE | 43 08 913 A1 | 9/1993 |
| DE | 196 23 788 A1 | 12/1997 |
| EP | 0 771 576 A2 | 5/1997 |
| EP | 0 872 261 A2 | 10/1998 |

*Primary Examiner*—Kennedy Schaetzle
(74) *Attorney, Agent, or Firm*—Hahn Loeser + Parks LLP; Stephen L. Grant

(57) ABSTRACT

An electrically active medical implant has a circuit (5), at least one first battery (1) to supply low current, and a second battery (2) to supply high current into the circuit (5), and a control device (4) designed to disconnect the at least one first battery (1) from circuit (5), and to connect second battery (2) to circuit (5), where a capacitor (3) connected in a parallel arrangement with battery (1), where the capacitor can be charged by the first battery both during a first circuit status, during which the first battery is connected to circuit (5), and during a second circuit status, during which circuit (5) is connected only to second battery (2), where control device (4) again disconnects second battery (2) from circuit (5) at the end of the second circuit status, and connects the parallel arrangement consisting of first battery (1) and capacitor (3) to circuit (5) for further energy supply.

28 Claims, 2 Drawing Sheets

ELECTRICALLY ACTIVE MEDICAL IMPLANT

The present invention relates to an electrically active medical implant with a circuit, at least one first battery to generate a low current into the circuit, a second battery to generate a high current, and a control means to disconnect the at least one first battery from the circuit and to connect the second battery to the circuit.

BACKGROUND OF THE ART

Medical implants, especially defibrillators, usually use two batteries as energy source. The first battery is designed to be a battery of low rate (the rate equals the amount of the charge and discharge current quantities related to the capacity of the battery, over a certain time period) and of a high storage capacity. On the contrary, the second battery is designed to be a battery of high rate and of a lower storage capacity. The battery with lower rate is used for normal monitoring and pacemaker functions, which require a current of the magnitude of about 10 $\mu$A, whereas the battery with high rate is applied to such activities as, e.g., the operation of a microprocessor and for therapy applications. During such activities with a high rate the required current is within the range between 200 $\mu$A and 1.5 A.

The battery with a low rate is typically a lithium iodide battery (LiI), whereas the battery with a high rate is a lithium-silver-vanadium oxide (SVO) battery or a lithium manganese oxide battery. The energy density (mAh per cm$^3$) of a LiI battery, i.e., a battery with low rate, is typically double the energy density of a battery with a high rate.

However, since activities with a high rate are rare, the battery with a low rate is used most of the time. The switching to the battery with a high rate occurs when the voltage of the battery with a low rate falls under a pre-set voltage due to the internal resistance of the battery.

The service life of the implant is determined by the combined service lives of the battery with a low rate and the battery with a high rate. However, this applies only to the monitoring function. If a therapy or other activities with a high rate are required, the current quantity used during such activity must be taken into account (deducted from the capacity of the battery with a high rate) when determining the service life of the battery with a high rate.

Every battery contains more chemical energy than a circuit can extract. As the depletion of the battery grows, the internal resistance of the battery increases up to a point, at which the voltage decrease at the internal resistance (current x resistance) causes that the output voltage of the battery falls under the minimum voltage value useable by the circuit.

U.S. Pat. No. 6,044,295 discloses a medical implant comprising a first battery for components that require a low current, a second battery for components that require a high current, and a switching device. The switching device connects the second battery to a second therapeutic unit only while a control signal is transmitted that indicates that a pre-set voltage level of the first battery is not reached, or that the internal resistance has exceeded a specific value. Then the switching device connects the second battery also with a first therapeutic unit.

U.S. Pat. No. 6,008,625 discloses a medical implant with two batteries. The first battery operates the medical implant both in the monitoring mode, for example, when monitoring the heart beat frequency, and in the mode of charging the capacitors, which require an electrical discharge with a high rate. When the first battery is discharged down to a certain pre-set voltage level, the first battery is afterwards used only for the monitoring function. From this time on, the second battery is also used for electrical pulse discharges with a high rate. When the first battery is depleted down to a certain pre-set level, the second battery takes over both the monitoring of the implant and other the operation functions.

In both aforementioned documents, a battery is disconnected from the remaining circuit, when its output voltage falls under a certain pre-set voltage. The disadvantage of this procedure consists in the fact that the energy remaining in the battery at this point can not be used any more.

U.S. Pat. No. 5,814,075 discloses an ICD (implantable cardioverter/defibrillator) comprising two different batteries which are alternately switched on according to a theorem of the fuzzy rules. The rules are to be selected in such a manner as to optimally utilize both batteries, and an explantation is not required by the mere fact that one of the two batteries is depleted. The disadvantage consists in a costly control of the switching process.

European Patent application No. 0 771 576 discloses an ICD, in which the output voltages of two batteries are fed to a control through various voltage busses.

SUMMARY OF THE INVENTION

The object of this invention is to design an alternate medical implant that uses the energy present in the batteries to a maximum extent.

This invention resolves the task with an electrically active medical implant according to claim 1.

The underlying idea of this invention is to design an electrically active medical implant with a circuit, a first battery and a second battery to produce a low current and a high current into the circuit, and a control device to disconnect the first battery from the circuit and to connect the second battery to the circuit. A capacitor connected in parallel arrangement with the first battery is further charged by this battery during a first and a second circuit status. During the first circuit status only the first battery is connected to the circuit, during the second circuit status only the second battery is connected to the circuit. At the end of the second circuit status the second battery is again disconnected from the circuit by the control device, and the parallel arrangement consisting of the first battery and the capacitor is again connected to continue the energy supply of the circuit.

The advantage inherent to this invention consists especially in the fact that current can be extracted from the battery with the low rate - and fed into the implant—beyond the point, where the output voltage of the battery under normal load conditions would fall below the pre-set voltage level.

In a design version of the invention, in the first circuit status the circuit is supplied with energy from the parallel arrangement consisting of the first battery and the capacitor, whereas during the second circuit status it is the second battery that supplies energy. The first circuit status ends and the second circuit status begins when the voltage of the parallel arrangement falls under a pre-set voltage level. This procedure ensures that the voltage of the parallel arrangement is at least at a level required to supply the circuit.

In another version of this invention the second circuit status ends and the first circuit status starts again, when the voltage in the parallel arrangement is again regenerated, and exceeds the limit value by a certain pre-set amount. In other words, the second battery is connected to the circuit only until the voltage of the parallel arrangement consisting of the first battery and a capacitor is recovered or rather regenerated, and can again serve as a voltage source for the circuit.

In an especially preferred version of this invention, the second circuit status lasts until the voltage of the parallel circuit reaches approximately the battery voltage or the no-load voltage of the first battery. This process ensures that the first battery has enough time to re-load the capacitor.

In yet another preferred design version of this invention, the control device comprises a sensor to record the voltage of the parallel circuit at pre-set intervals. This process ensures that the voltage level in the parallel circuit is monitored at pre-set intervals so that the control device may connect the first battery to the circuit again, if possible.

Further design versions of the inventions are the subject of subclaims.

BRIEF DESCRIPTION OF THE DRAWINGS

The text will be best understood when reference is made to the accompanying drawings, wherein.

DETAILED DESCRIPTION OF THE INVENTION

Figure 1:
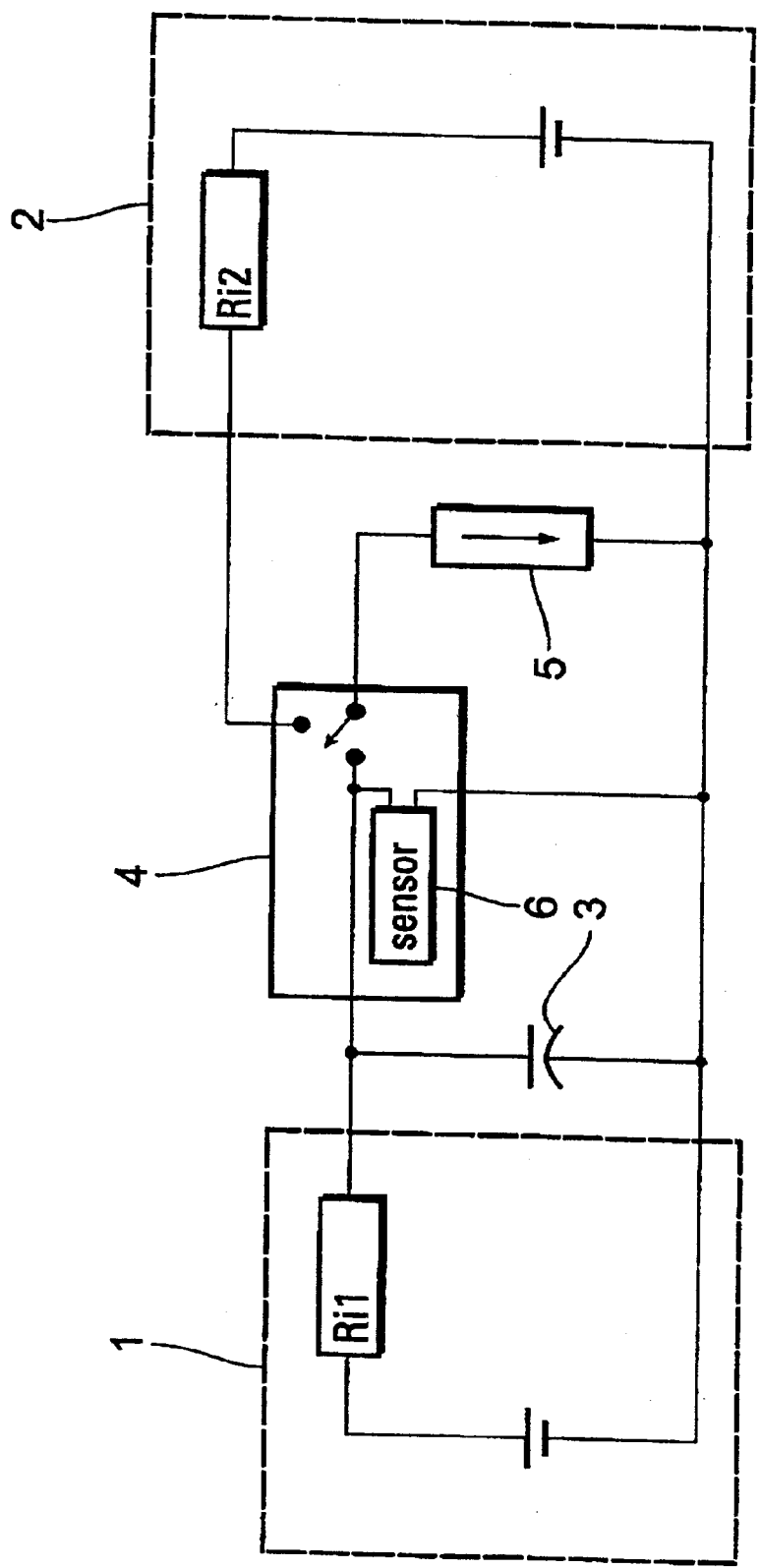
FIG. 1 shows a schematic circuit diagram to control energy supply of a medical implant.

FIG. 1 shows a schematic circuit diagram to control energy supply of a medical implant. The medical implant comprises at least one first battery 1, a second battery 2, a capacitor 3, a switch 4, a voltage sensor 6, and conventional circuit components 5 of the medical implant.

When sensor 6 records that the output voltage of the at least one first battery falls under a first pre-set voltage level, swicth 4 is actuated to disconnect the at least one first battery from circuit 5 and to connect the second battery to circuit 5 so that the second battery supplies circuit 5 with the necessary current. During this second circuit status, in which the at least one first battery is disconnected from circuit 5 and the second battery 2 is connected to the circuit, the capacitor obtains the entire available current from at least one first battery 1.

During the current consumption from at least one first battery 1, a voltage decrease occurs—first slower and then faster at the end of the discharge. If the discharge is interrupted, the voltage immediately increases again and slowly grows again in the ensuing no-load condition. The battery "recovers".

The level of the voltage in the parallel circuit consisting of at least one first battery 1 and capacitor 3 is monitored by sensor 6 at regular intervals. As soon as this voltage increases to the pre-set level or exceeds this pre-set level by a certain amount, which is required for a regular operation of circuit 5, switch 4 is actuated to disconnect second battery 2 from circuit 5, and to connect the parallel circuit consisting of at least one first battery 1 and capacitor 3 to circuit 5, which represents again the first circuit status. The capacitor, together with at least one first battery 1 supplies circuit 5 with the required current until the voltage in the parallel circuit falls under the voltage level required by circuit 5.

Figure 2:
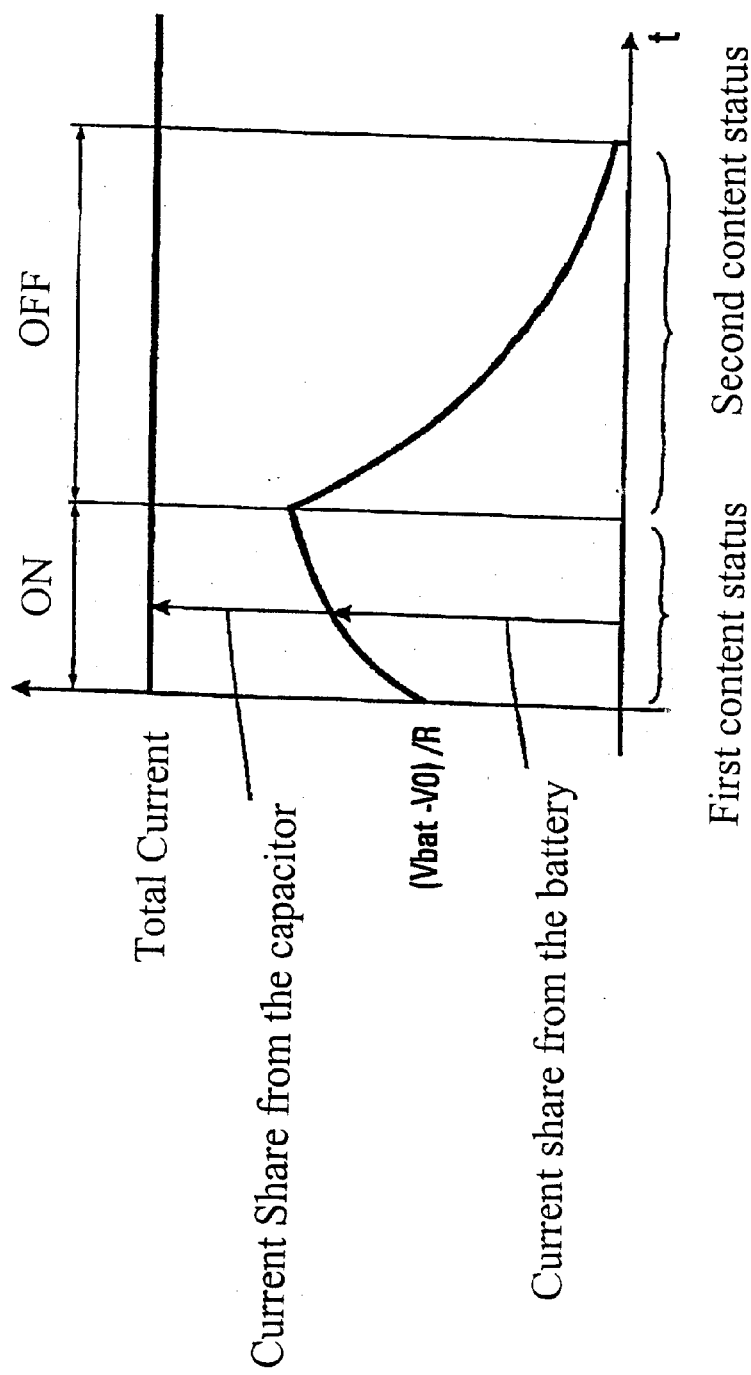
FIG. 2 shows a graphic illustration of the battery and capacitor current.

FIG. 2 illustrates the currents supplied by at least one first battery 1 and capacitor 3. Vbat designates the no-load voltage of the at least one first battery and V0 designates the voltage over the capacitor at the end of the second circuit status. The impedance of the battery is marked with R. ON designates the first circuit status, and OFF designates the second circuit status.

When in the course of time the battery depletes, the first circuit status becomes shorter a capacitor 3 is no longer in a position to be charged to the full Vbat voltage. The consequence is that the initial current [(Vbat-V0)/R] shown in FIG. 2 becomes smaller, since the value of the internal impedance R of the battery grows.

When the voltage of the parallel circuit again falls under the voltage threshold value, switch 4 disconnects the parallel circuit consisting of at least one first battery 1 and capacitor 3 from circuit 5, and connects second battery 2 again to circuit 5 (second circuit status). During this phase, the capacitor is again charged to a higher charge value, to which at least one first battery 1 recovers, since during this circuit status the circuit, i.e., a corresponding load is not connected. When the voltage in the parallel circuit increases again over the pre-set voltage threshold value, i.e., over the voltage required to supply circuit 5, second battery 2 is again disconnected from circuit 5, and the parallel circuit consisting of at least one first battery 1 and the capacitor is again connected to the circuit (first circuit status).

During the second circuit status, i.e. when the parallel circuit consisting of at least one first battery 1 and capacitor 3 is disconnected from circuit 5, the internal resistance of battery 1 and capacitor 3 form an RC circuit. It means that the voltage over the internal resistance of the at least one first battery decreases, while capacitor 3 is charged by the battery, until the voltage at the capacitor equals the no-load voltage of the at least one first battery. As the battery depletes, the no-load voltage of the at least one first battery becomes smaller than its original no-load voltage. The consequence is that the capacitor, too, can no longer be charged to the initial no-load voltage of at least one first battery 1. At some point, the depletion of the battery reaches such a level that the voltage obtained by charging capacitor 3 is smaller than the voltage required for circuit 5.

FIG. 1 shows a circuit that represents the principle of a charge pump, which attempts to extract the remaining charge capacity from the at least one first battery beyond the point, at which at least one first battery 1 still manages to supply circuit 5 with continuous current.

The capacitor 3 is designed relatively large and has preferably a capacity of 68 micro farad.

What is claimed is:

1. An electrically active medical implant, comprising:
   a circuit,
   at least one first battery to supply low current to the circuit,
   a second battery to supply high current to the circuit,
   a control device to disconnect said at least one first battery from the circuit, and to connect the second battery to the circuit, and
   a capacitor connected in parallel with said at least one first battery, such that the capacitor can be charged by said at least one first battery during a first circuit status, during which said at least one first battery is connected to the circuit, and during a second circuit status, during which the circuit is connected only to the second battery,
   wherein the control device again disconnects the second battery from the circuit at an end of the second circuit status, and connects said at least one first battery in parallel to the capacitor and to the circuit for further energy supply.

2. The medical implant of claim 1, wherein:
   the first circuit status ends and the second circuit status begins when a voltage of the parallel connection of said at least one first battery and the capacitor falls below a pre-set threshold voltage value.

3. The medical implant of claim 2, wherein: the second circuit status ends and the first circuit status begins when the voltage of the parallel connection of said at least one first battery and the capacitor exceeds the threshold voltage value by a pre-set amount.

4. The medical implant of claim 3, wherein: the second circuit status lasts until the voltage of the parallel connection of said at least one first battery and the capacitor reaches approximately the battery voltage or the no-load voltage of said at least one first battery.

5. The medical implant of claim 4, wherein: the control device repeatedly alternates the circuit between the first and second circuit status.

6. The medical implant of claim 5, wherein the control device comprises:
a sensor to record the voltage in the parallel connection at pre-set time intervals.

7. The medical implant of claim 6, wherein the control device further comprises:
a switch for connecting and disconnecting said at least one first battery and the second battery from the circuit.

8. The medical implant of claim 7, wherein the capacitor has a capacity of at least about 68 $\mu$F.

9. The medical implant of claim 8, wherein: said at least one first battery has lower performance but has a high storage capacity, when compared to the second battery.

10. The medical implant of claim 3, wherein: the control device repeatedly alternates the circuit between the first and second circuit status.

11. The medical implant of claim 10, wherein the control device comprises:
a sensor to record the voltage in the parallel connection at pre-set time intervals.

12. The medical implant of claim 11, wherein the control device further comprises:
a switch for connecting and disconnecting said at least one first battery and the second battery from the circuit.

13. The medical implant of claim 12, wherein the capacitor has a capacity of at least about 68 $\mu$F.

14. The medical implant of claim 13, wherein: said at least one first battery has lower performance but has a high storage capacity, when compared to the second battery.

15. The medical implant of claim 2, wherein: the control device repeatedly alternates the circuit between the first and second circuit status.

16. The medical implant of claim 15, wherein the control device comprises:
a sensor to record the voltage in the parallel connection at pre-set time intervals.

17. The medical implant of claim 16, wherein the control device further comprises:
a switch for connecting and disconnecting said at least one first battery and the second battery from the circuit.

18. The medical implant of claim 17, wherein the capacitor has a capacity of at least about 68 $\mu$F.

19. The medical implant of claim 18, wherein: said at least one first battery has lower performance but has a high storage capacity, when compared to the second battery.

20. The medical implant of claim 1, wherein: the control device repeatedly alternates the circuit between the first and second circuit status.

21. The medical implant of claim 20, wherein the control device comprises:

a sensor to record the voltage in the parallel connection at pre-set time intervals.

22. The medical implant of claim 21, wherein the control device further comprises:
a switch for connecting and disconnecting said at least one first battery and the second battery from the circuit.

23. The medical implant of claim 22, wherein the capacitor has a capacity of at least about 68 $\mu$F.

24. The medical implant of claim 23, wherein: said at least one first battery has lower performance but has a high storage capacity, when compared to the second battery.

25. The medical implant of claim 1, wherein the capacitor has a capacity of at least about 68 $\mu$F.

26. The medical implant of claim 25, wherein: said at least one first battery has lower performance but has a high storage capacity, when compared to the second battery.

27. The medical implant of claim 1, wherein: said at least one first battery has lower performance but has a high storage capacity, when compared to the second battery.

28. An electrically active medical implant, comprising:
a circuit,
at least one first battery to supply low current to the circuit,
a second battery to supply high current to the circuit,
a capacitor connected in parallel with said at least one first battery, such that the capacitor can be charged by said at least one first battery during a first circuit status, during which said at least one first battery is connected to the circuit, and during a second circuit status, during which the circuit is connected only to the second battery, and
a control device to disconnect said at least one first battery from the circuit, and to connect the second battery to the circuit, the control device comprising:
a sensor to record the voltage in the parallel connection at pre-set time intervals; and
a switch for connecting and disconnecting said at least one first battery and the second battery from the circuit;
wherein the control device again disconnects the second battery from the circuit at an end of the second circuit status, and connects said at least one first battery in parallel to the capacitor and to the circuit for further energy supply;
wherein the first circuit status ends and the second circuit status begins when a voltage of the parallel connection of said at least one first battery and the capacitor falls below a pre-set threshold voltage value; wherein the second circuit status ends and the first circuit status begins when the voltage of the parallel connection of said at least one first battery and the capacitor exceeds the threshold voltage value by a pre-set amount;
wherein the second circuit status lasts until the voltage of the parallel connection of said at least one first battery and the capacitor reaches approximately the battery voltage or the no-load voltage of said at least one first battery;
wherein the control device repeatedly alternates the circuit between the first and second circuit status; and
wherein the capacitor has a capacity of at least about 68 $\mu$F.

* * * * *